(12) United States Patent
Chin et al.

(10) Patent No.: US 11,247,028 B2
(45) Date of Patent: Feb. 15, 2022

(54) DEVICE FOR GLOBAL AND TARGETED DELIVERY OF BRACHYTHERAPY TO THE BLADDER LUMEN

(71) Applicant: THE REGENTS OF THE UNIVERSITY OF CALIFORNIA, Oakland, CA (US)

(72) Inventors: Robert Chin, Los Angeles, CA (US); Mitchell Kamrava, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 299 days.

(21) Appl. No.: 15/768,621

(22) PCT Filed: Oct. 17, 2016

(86) PCT No.: PCT/US2016/057370
§ 371 (c)(1),
(2) Date: Apr. 16, 2018

(87) PCT Pub. No.: WO2017/066773
PCT Pub. Date: Apr. 20, 2017

(65) Prior Publication Data
US 2018/0311483 A1    Nov. 1, 2018

Related U.S. Application Data

(60) Provisional application No. 62/242,634, filed on Oct. 16, 2015.

(51) Int. Cl.
*A61M 25/10* (2013.01)
*A61F 7/12* (2006.01)
(Continued)

(52) U.S. Cl.
CPC ......... *A61M 25/1009* (2013.01); *A61F 7/123* (2013.01); *A61M 25/1002* (2013.01); *A61N 5/1014* (2013.01); *A61F 2007/0059* (2013.01); *A61F 2007/126* (2013.01); *A61M 2210/1085* (2013.01); *A61N 2005/1003* (2013.01);
(Continued)

(58) Field of Classification Search
CPC .......... A61M 25/1002; A61M 25/1009; A61M 2025/1059; A61M 2025/1065; A61M 2025/1068; A61M 2210/1085; A61N 5/1014–1017; A61N 2005/1018; A61N 2005/1003; A61N 2005/1004; A61F 7/123; A61F 2007/126
See application file for complete search history.

(56) References Cited

U.S. PATENT DOCUMENTS 5,653,683 A * 8/1997 D'Andrea ............ A61N 5/1014
600/2
5,961,536 A * 10/1999 Mickley ................ A61M 25/10
604/96.01
(Continued)

*Primary Examiner* — Catherine B Kuhlman
(74) *Attorney, Agent, or Firm* — Riverside Law LLP

(57) ABSTRACT

The present invention provides balloon catheters and methods for using the same. Unlike existing balloon catheters in the art, the present balloon catheters expand in the proximal direction to enhance fit. The balloon catheters include sliding balloon catheters, preformed balloon catheters, superelastic balloon catheters, and may be augmented with peripheral catheters.

19 Claims, 19 Drawing Sheets

(51) Int. Cl.
*A61N 5/10* (2006.01)
*A61F 7/00* (2006.01)

(52) U.S. Cl.
CPC ............... *A61N 2005/1004* (2013.01); *A61N 2005/1022* (2013.01); *A61N 2005/1024* (2013.01); *A61N 2005/1091* (2013.01)

(56) References Cited

U.S. PATENT DOCUMENTS

| | | | |
|---|---|---|---|
| 8,715,228 B2* | 5/2014 | Barki | A61M 25/0021 604/96.01 |
| 10,238,842 B2* | 3/2019 | Gobel | A61M 3/0295 |
| 2006/0100475 A1* | 5/2006 | White | A61N 5/1015 600/3 |
| 2006/0173235 A1* | 8/2006 | Lim | A61N 5/1016 600/6 |
| 2008/0177127 A1* | 7/2008 | Allan | A61M 25/1002 600/7 |
| 2009/0018383 A1* | 1/2009 | Corcione | A61N 5/1015 600/7 |
| 2015/0091221 A1* | 4/2015 | Connolly | A61M 25/1029 264/515 |

* cited by examiner

DEVICE FOR GLOBAL AND TARGETED DELIVERY OF BRACHYTHERAPY TO THE BLADDER LUMEN

CROSS-REFERENCE TO RELATED APPLICATIONS

This application is the U.S. national phase application filed under 35 U.S.C. § 371 claiming benefit to International Patent Application No. PCT/US16/57370, filed Oct. 17, 2016, which is entitled to priority under 35 U.S.C. § 119(e) to U.S. Provisional Patent Application No. 62/242,634, filed Oct. 16, 2015, the contents of which are each incorporated herein by reference in their entirety.

BACKGROUND OF THE INVENTION 60,000 patients are diagnosed with bladder cancer annually, with the majority of these patients presenting with early disease. Currently, bladder cancer is treated with transurethral resection with or without subsequent intra-bladder immunotherapy. Unfortunately, the recurrence rate is quite high, and often in other areas of the bladder. This requires additional resections, and in many cases full surgical removal of the bladder.

Radiotherapy can be effective treatment for bladder cancer patients, but its use is limited by perceived toxicity associated with the radiation beam needing to traverse the entire pelvis before depositing dose within the bladder lumen, and difficulty in targeting an organ where shape, size, and location can change hourly, leading to overtreatment, misses, and often both in the same patient.

There is a need in the art for improved devices for administering treatment to the bladder. The present invention meets this need.

SUMMARY OF THE INVENTION

The present invention provides balloon catheters and methods for using the same. Unlike existing balloon catheters in the art, the present balloon catheters expand in the proximal direction to enhance fit. The balloon catheters include sliding balloon catheters, preformed balloon catheters, super-elastic balloon catheters, tip-loaded balloon catheters, and the balloon catheters may be augmented with peripheral catheters.

In one aspect, the invention relates to a sliding balloon catheter device. The device comprises: an inflation tube having a lumen, a distal end and a proximal end; at least one catheter positioned within the lumen of the inflation tube sharing a distal end with the inflation tube; and an elastic balloon at least partially attached along its length to the distal end of the inflation tube and is fluidly connected to the inflation tube; wherein the balloon is expanded proximally along the catheter.

In one embodiment, the device further comprises a semirigid sliding ring attached to the proximal end of the balloon that encircles the exterior of the inflation tube. In one embodiment, the sliding ring has an adjustable circumference. In one embodiment, the device further comprises a ring adjustment member attached to the sliding ring. In one embodiment, the device further comprises at least one peripheral catheter attached to the exterior of the balloon.

In one embodiment, the balloon comprises a material selected from the group consisting of: rubber, silicone, nylon, polyethylene terephthalate (PET), and polyurethane. In one embodiment, the balloon comprises a uniform material thickness. In one embodiment, the balloon comprises one or more regions of varying material thickness. In one embodiment, the balloon, the inflation tube, and the at least one catheter are fluidly connected.

In another aspect, the invention relates to a preformed balloon catheter device comprising: an inflation tube having a lumen, a distal end and a proximal end; at least one catheter positioned within the lumen of the inflation tube sharing a distal end with the inflation tube; and an inelastic balloon at least partially attached along its length to the distal end of the inflation tube and is fluidly connected to the inflation tube; wherein the balloon is expanded proximally along the catheter.

In another aspect, the invention relates to a super-elastic balloon catheter device comprising: an inflation tube having a lumen, a distal end and a proximal end; at least one catheter positioned within the lumen of the inflation tube sharing a distal end with the inflation tube; and a highly elastic balloon attached along its length to the distal end of the inflation tube and is fluidly connected to the inflation tube; wherein the balloon is expanded proximally along the catheter. In one embodiment, the balloon conforms to the shape of a body cavity when fully inflated.

In another aspect, the invention relates to a tip-loaded balloon catheter device, comprising: an inflation tube having a lumen, a distal end, a distal tip, and a proximal end; at least one catheter positioned within the lumen of the inflation tube; a balloon attached at the distal tip of the inflation tube and is fluidly connected to the inflation tube. In one embodiment, the balloon is a preformed, substantially inelastic balloon. In one embodiment, the balloon is a super-elastic balloon that conforms to the shape of a body cavity when fully inflated.

In another aspect, the invention relates to a method of inserting a balloon catheter into a body cavity, comprising the steps of: inserting the distal end of a balloon catheter having an inflation tube and at least one catheter into the body cavity; positioning the balloon catheter in the body cavity such that the distal end is in contact with the body cavity wall opposite the body cavity entry point; inflating the balloon with a fluid using the inflation tube; and expanding the balloon proximally to fill the body cavity.

In one embodiment, the fluid is one of a liquid or a gas. In one embodiment, the balloon catheter further comprises a sliding ring and a ring adjustment member. In one embodiment, the method further comprises the step of applying tension on a ring adjustment member such that the sliding ring increases the proximal expansion of the balloon. In one embodiment, the balloon catheter further comprises at least one peripheral catheter. In one embodiment, the method further comprises the step of rotating the balloon catheter such that the at least one peripheral catheter is positioned adjacent to a site requiring treatment. In one embodiment, the method further comprises the step of inserting medical instruments into the at least one catheter positioned near a site requiring treatment. In one embodiment, the treatment is selected from the group consisting of: radiotherapy, thermotherapy, chemotherapy, laparoscopy, drug delivery, and immunotherapy. In one embodiment, the at least one medical instrument is selected from the group consisting of: a radiotherapy pellet, an imaging device, a syringe, and a microsurgical device.

In another aspect, the invention relates to a method of inserting a balloon catheter into a bladder, comprising the steps of: inserting the distal end of a balloon catheter having an inflation tube and at least one catheter into the bladder through the urethra or a suprapubic puncture; positioning the balloon catheter in the bladder such that the distal end is in contact with the bladder wall opposite the bladder entry point; inflating the balloon with a fluid using the inflation tube; and expanding the balloon proximally to fill the bladder.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
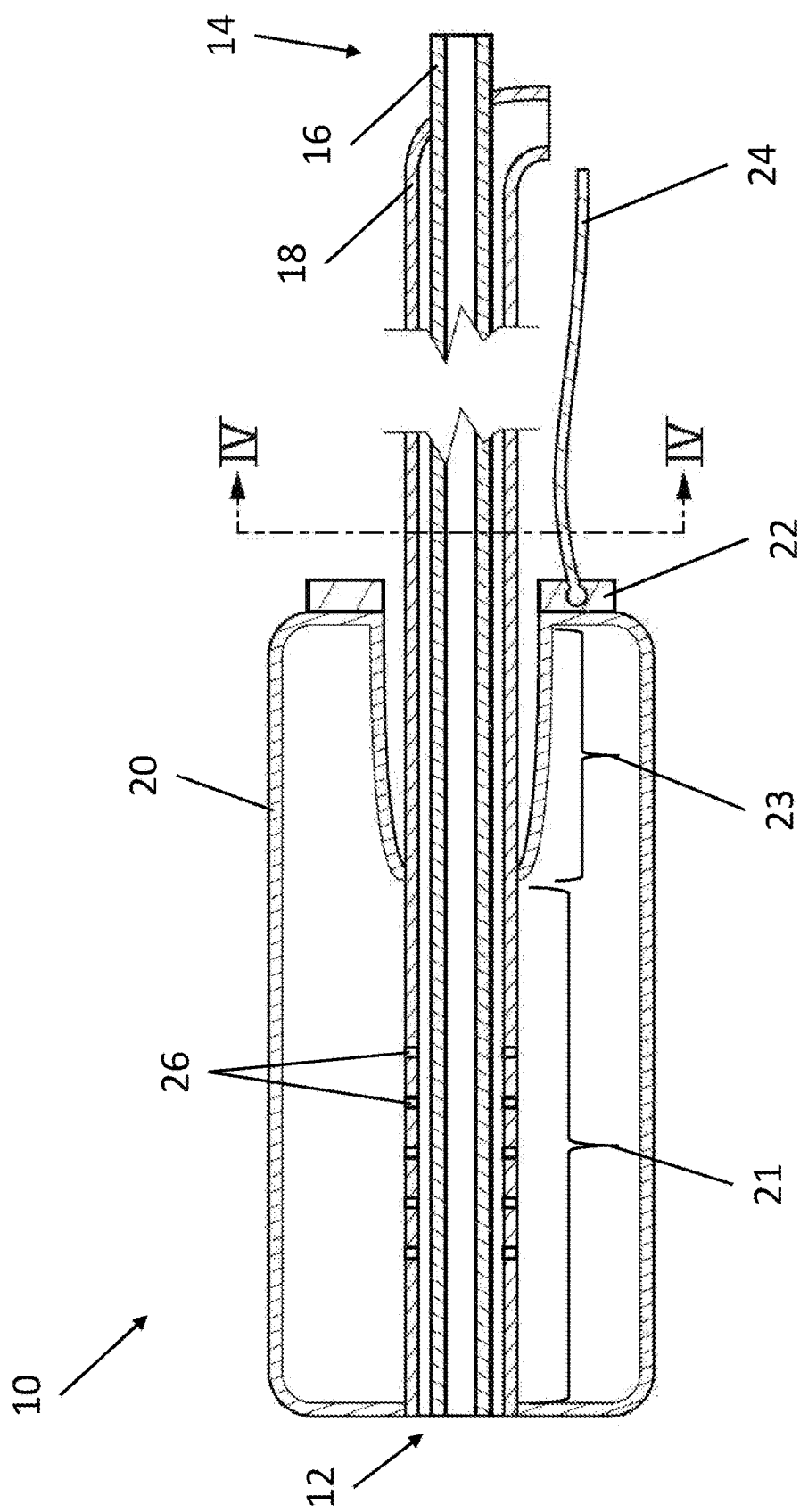
FIG. 1 depicts a side cross section view of an exemplary sliding balloon catheter in a partially collapsed configuration.

The present invention provides balloon catheters and methods for using the same. Unlike existing balloon catheters in the art, the present balloon catheters expand in the proximal direction to enhance fit. The balloon catheters include sliding balloon catheters, preformed balloon catheters, super-elastic balloon catheters, and may be augmented with peripheral catheters.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

The present invention provides balloon catheters and methods for using the same. Unlike existing balloon catheters in the art, the present balloon catheters expand in the proximal direction to enhance fit. The balloon catheters include sliding balloon catheters, preformed balloon catheters, super-elastic balloon catheters, and may be augmented with peripheral catheters. In certain embodiments, the balloon catheters provide a superior method of performing a treatment or medical procedure to a localized site, such as delivering localized doses of radiation to the bladder urothelium, by being able to expand to a size larger than the body cavity it is inserted in to provide coverage to all body cavity surfaces.

Sliding Balloon Catheter

Referring now to FIG. 1, an exemplary sliding balloon catheter 10 is depicted. Sliding balloon catheter 10 has a distal end 12 and a proximal end 14 and comprises catheter 16, inflation tube 18, and sliding balloon 20. In certain embodiments, sliding balloon 20 comprises sliding ring 22 and ring adjustment member 24. Inflation tube 18 is fluidly connected to sliding balloon 20 by a plurality of apertures 26.

Catheter 16 fits within the lumen of inflation tube 18. Catheter 16 is dimensioned to fit any suitable medical instrument, such as radiotherapy pellets, imaging devices, syringes, microsurgical devices, and the like. Catheter 16 may be open or closed at its distal end.

Sliding balloon 20 can comprise any suitable material that can withstand pressure from being inflated. For example, sliding balloon 20 may comprise materials including but not limited to: rubber, silicone, nylon, polyethylene terephthalate (PET), polyurethane, and the like. In one embodiment, sliding balloon 20 can have a substantially uniform material thickness. In another embodiment, sliding balloon 20 can have one or more regions of varying thickness, such that thinner regions have greater elasticity and thicker regions have less elasticity to promote directional expansion as desired. For example, sliding balloon 20 can have proximal regions comprising a thinner material than distal regions to promote directional expansion in the proximal direction.

Figure 4:
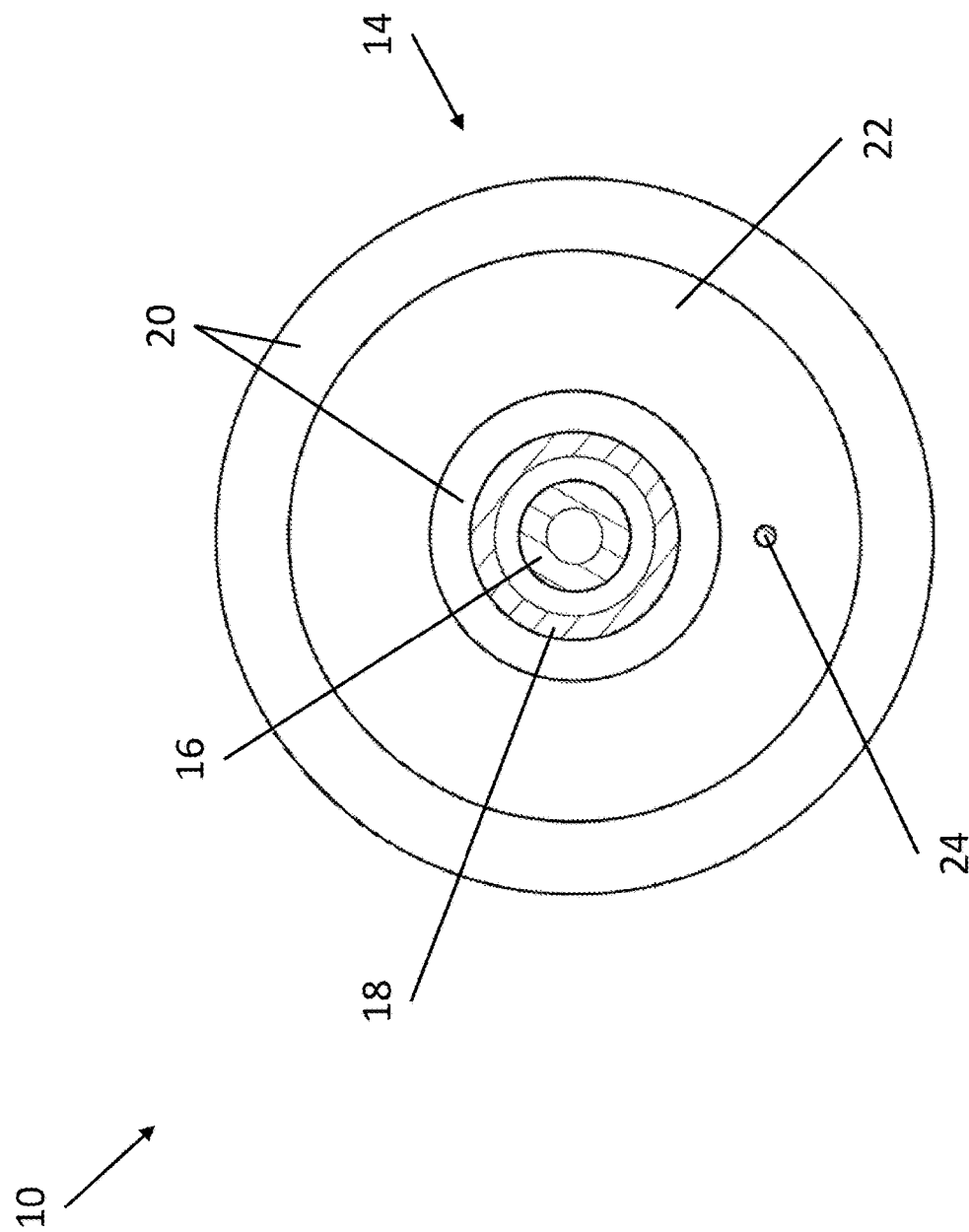
FIG. 4 depicts a proximal cross section view of an exemplary sliding balloon catheter in a partially collapsed configuration.

Sliding balloon 20 is positioned at the distal end 12 of sliding balloon catheter 10. Sliding balloon 20 can be characterized as having a substantially donut shaped cross section (visible in FIG. 4) having an inner "donut hole" formed by the inner surface of sliding balloon 20. Sliding balloon 20 is attached to sliding balloon catheter 10 such that the distal portion 21 of its inner surface is joined to the distal outer surface of inflation tube 18. Sliding balloon 20 is inflated and deflated by inflation tube 18, wherein any suitable fluid (including but not limited to air, purified gas, water, saline and the like) enter and exit sliding balloon 20 through the plurality of apertures 26. In certain embodiments, sliding balloon 20 and inflation tube 18 are fluidly connected to catheter 16, such that fluids may be circulated through all three elements. For example, in certain embodiments wherein the fluid has a closely defined temperature, such as in thermotherapy, rapid circulation of fluid through sliding balloon 20, inflation tube 18, and catheter 16 enables the maintenance of the closely defined temperature.

Figure 2:
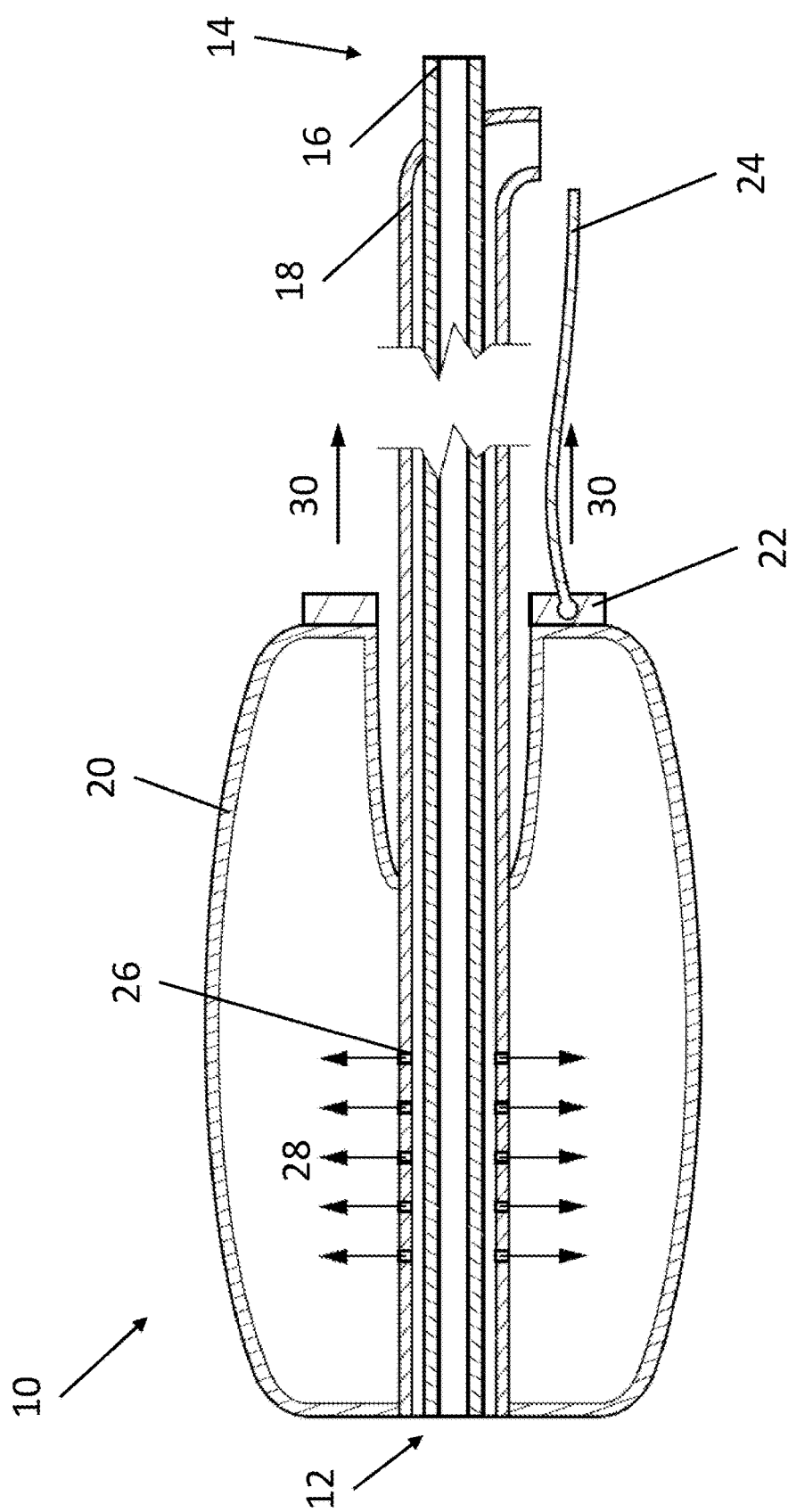
FIG. 2 depicts a side cross section view of an exemplary sliding balloon catheter in a partially deployed configuration.
Figure 3:
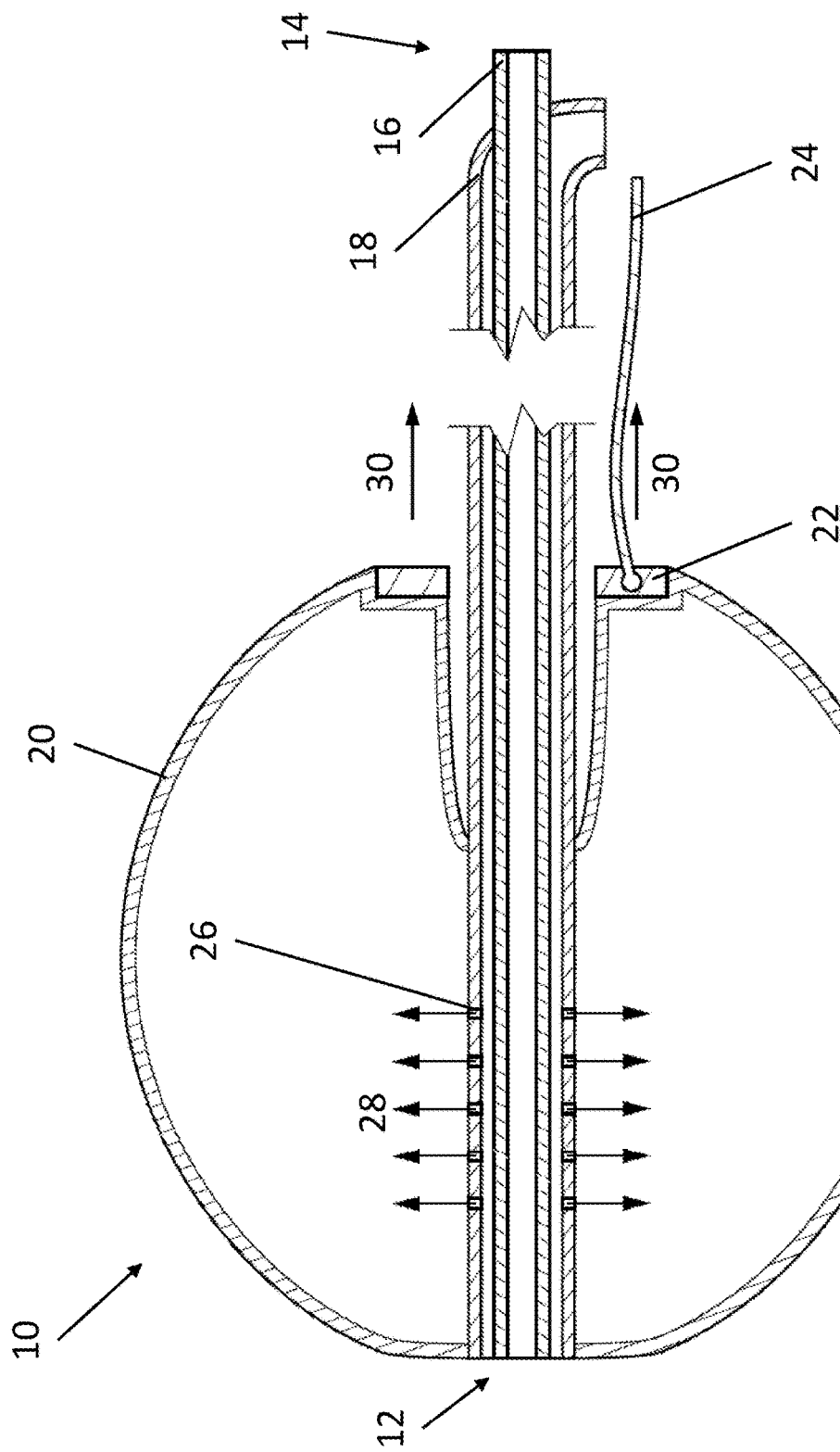
FIG. 3 depicts a side cross section view of an exemplary sliding balloon catheter in a fully deployed configuration.

Referring now to FIG. 2 and FIG. 3, inflating sliding balloon 20 causes lateral expansion 28 of sliding balloon 20. The proximal portion 23 of sliding balloon 20, being free from attachment to the outer surface of inflation tube 18, enables proximal expansion 30 when sliding balloon 20 is inflated. Sliding balloon 20 preferably expands while retaining a shape that is proportional to its original shape. For example, expanding sliding balloon 20 to double its diameter correspondingly increases the length of distal portion 23 by a similar factor. Sliding balloon 20 preferably does not expand in the distal direction.

In certain embodiments, sliding balloon 20 comprises a semi-rigid sliding ring 22 at its proximal end. Sliding ring 22 aids in maintaining the conformation of sliding balloon 20 as it expands. In certain embodiments, the proximal expansion 30 of sliding balloon 20 may be aided by ring adjustment member 24. For example, a tensile force exerted on ring adjustment member 24 in the proximal direction may enhance proximal expansion 30 of sliding balloon 20. In one embodiment, sliding ring 22 has an adjustable circumference, such that adjusting the circumference increases or decreases friction between sliding ring 22 and the exterior surface of inflation tube 18, thereby controlling the rate of proximal expansion.

Preformed Balloon Catheter

Figure 5:
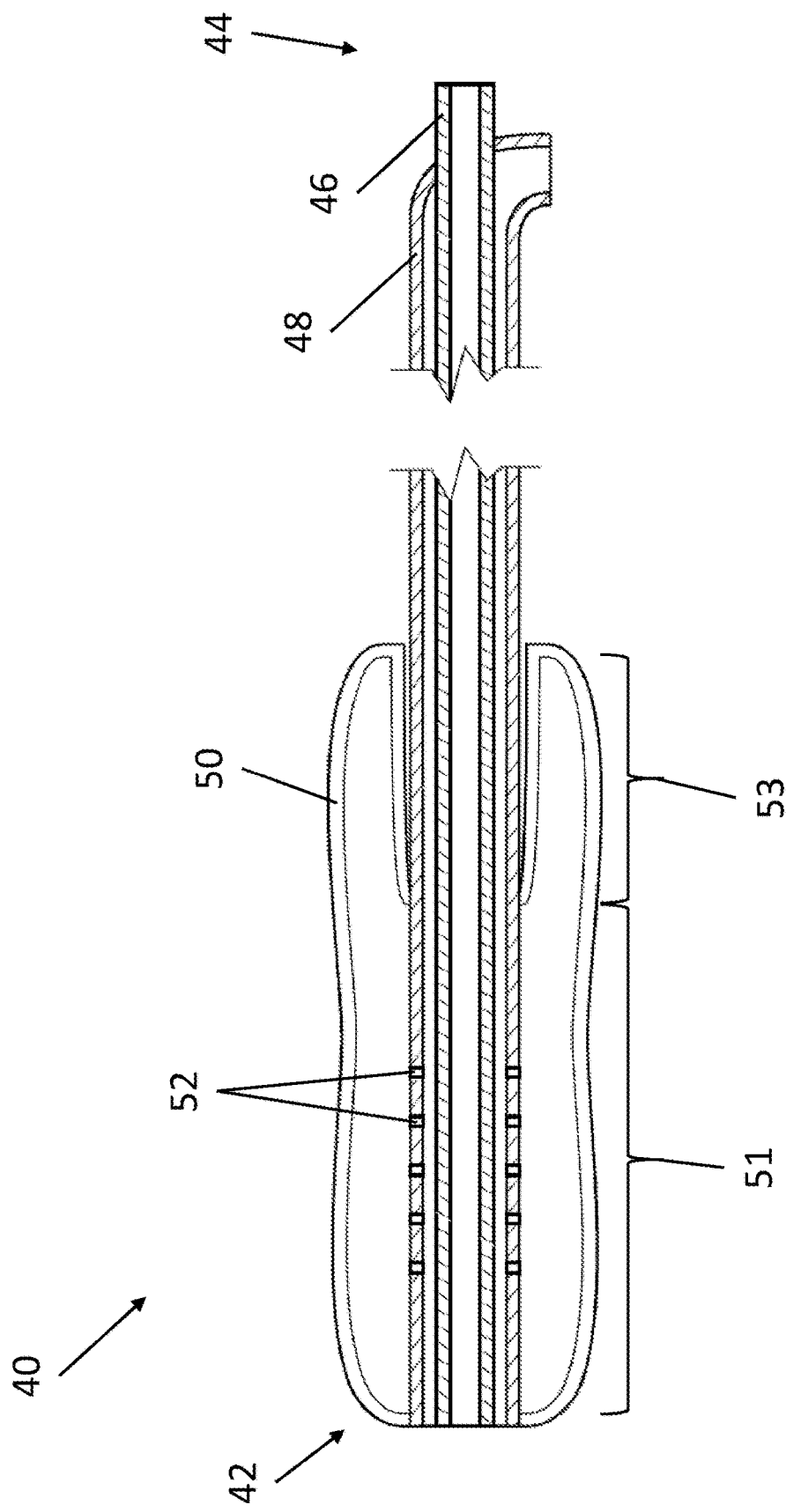
FIG. 5 depicts a side cross section view of an exemplary preformed balloon catheter in a partially collapsed configuration.

Referring now to FIG. 5, an exemplary preformed balloon catheter 40 is depicted. Preformed balloon catheter 40 has a distal end 42 and a proximal end 44 and comprises catheter 46, inflation tube 48, and preformed balloon 50. Inflation tube 48 is fluidly connected to preformed balloon 50 by a plurality of apertures 52.

Catheter 46 fits within the lumen of inflation tube 48. Catheter 46 is dimensioned to fit any suitable medical instrument, such as radiotherapy pellets, imaging devices, syringes, microsurgical devices, and the like. Catheter 46 may be open or closed at its distal end.

Preformed balloon 50 can comprise any suitable material that can withstand pressure from being inflated. For example, preformed balloon 50 may comprise materials including but not limited to: rubber, silicone, nylon, PET, polyurethane, and the like. Preformed balloon 50 is preferably molded to have a predetermined shape and retains its shape when expanded with minimal elasticity, so it may be advantageous for preformed balloon 50 to comprise an inelastic material such as Mylar, or to be molded in slightly thicker material. In one embodiment, preformed balloon 50 can have a substantially uniform material thickness. In another embodiment, preformed balloon 50 can have one or more regions of varying thickness, such that thinner regions have greater elasticity and thicker regions have less elasticity to promote directional expansion as desired. For example, preformed balloon 50 can have proximal regions comprising a thinner material than distal regions to promote directional expansion in the proximal direction.

Preformed balloon 50 is positioned at the distal end 42 of preformed balloon catheter 40. Preformed balloon 50 can be characterized as having a substantially donut shaped cross section having an inner "donut hole" formed by the inner surface of preformed balloon 50. Preformed balloon 50 is attached to preformed balloon catheter 40 such that the distal portion 51 of its inner surface is joined to the distal outer surface of inflation tube 48. Preformed balloon 50 is inflated and deflated by inflation tube 48, wherein any suitable fluid (including but not limited to air, purified gas, water, saline and the like) enter and exit preformed balloon 50 through the plurality of apertures 52. In certain embodiments, preformed balloon 50 and inflation tube 48 are fluidly connected to catheter 46, such that fluids may be circulated through all three elements. For example, in certain embodiments wherein the fluid has a closely defined temperature, such as in thermotherapy, rapid circulation of fluid through preformed balloon 50, inflation tube 48, and catheter 46 enables the maintenance of the closely defined temperature.

Figure 6:
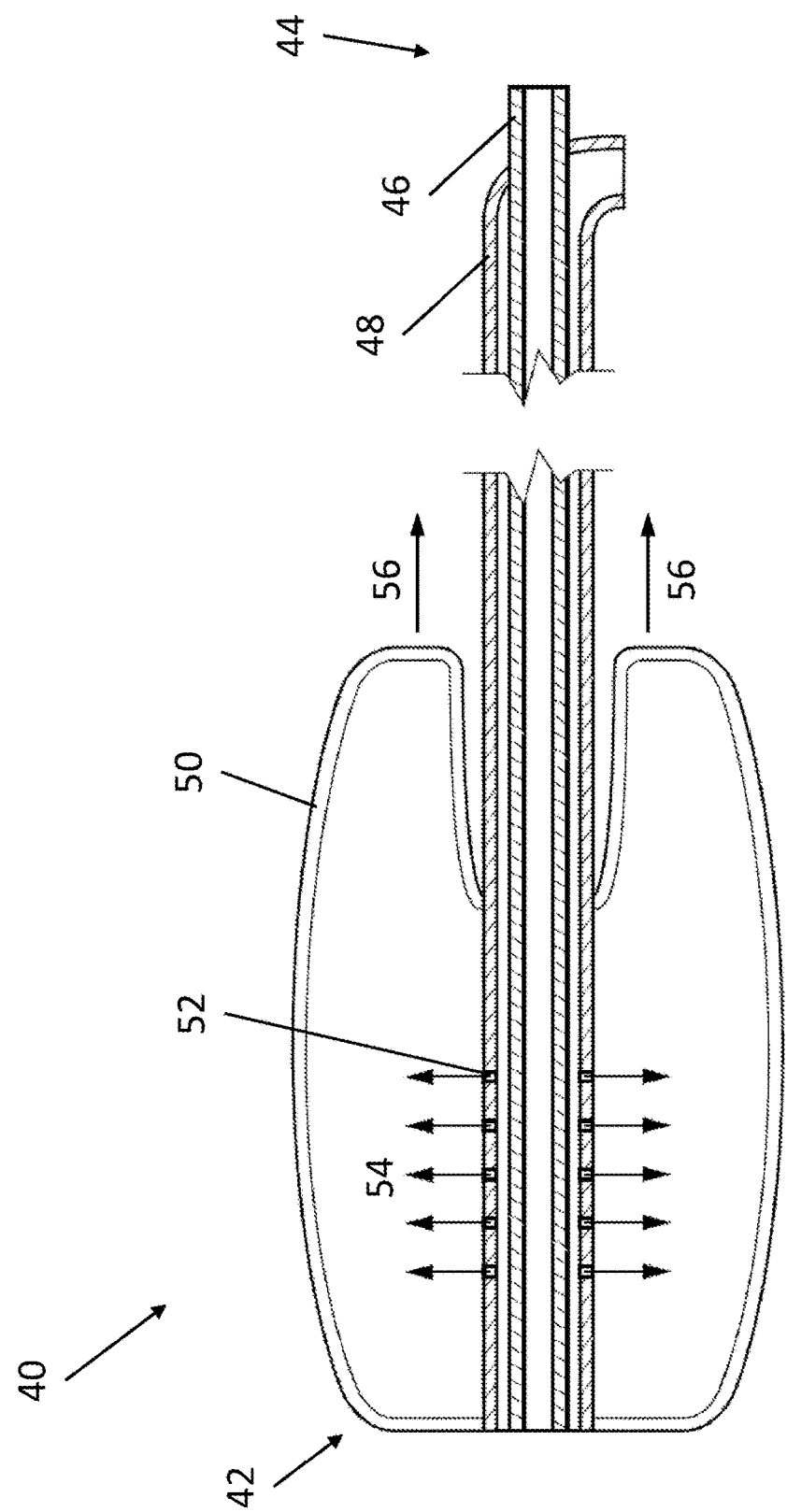
FIG. 6 depicts a side cross section view of an exemplary preformed balloon catheter in a partially deployed configuration.
Figure 7:
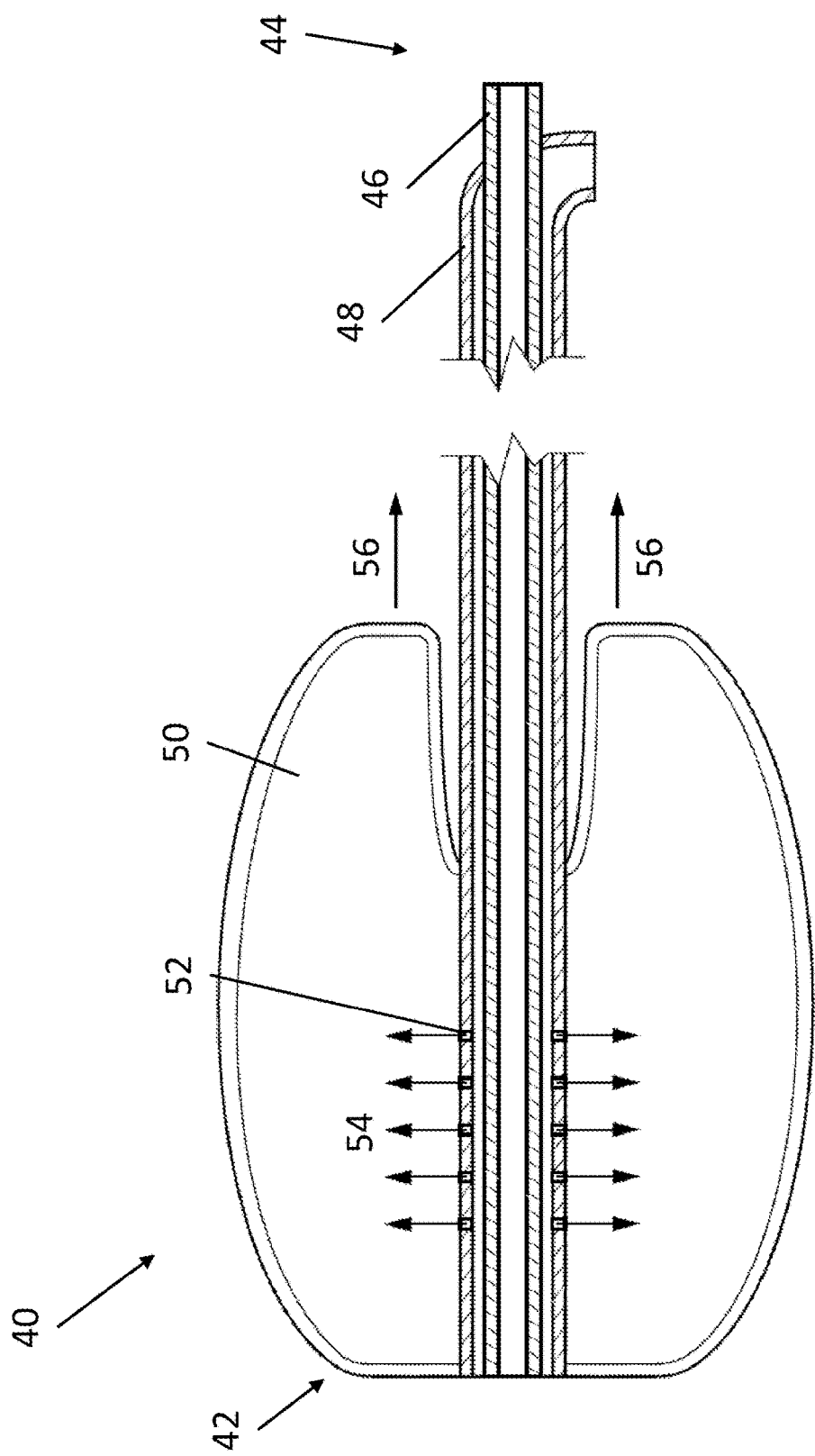
FIG. 7 depicts a side cross section view of an exemplary preformed balloon catheter in a fully deployed configuration.

Referring now to FIG. 6 and FIG. 7, inflating preformed balloon 50 causes lateral expansion 54 of preformed balloon 50. The proximal portion 53 of preformed balloon 50, being free from attachment to the outer surface of inflation tube 48, enables proximal expansion 56 when preformed balloon 50 is inflated. Due to the relatively inelastic nature (low compliance) of preformed balloon 50, the expansion is limited by the balloon's preformed shape. Preformed balloon 50 preferably does not expand in the distal direction.

Super-Elastic Balloon Catheter

Figure 8:
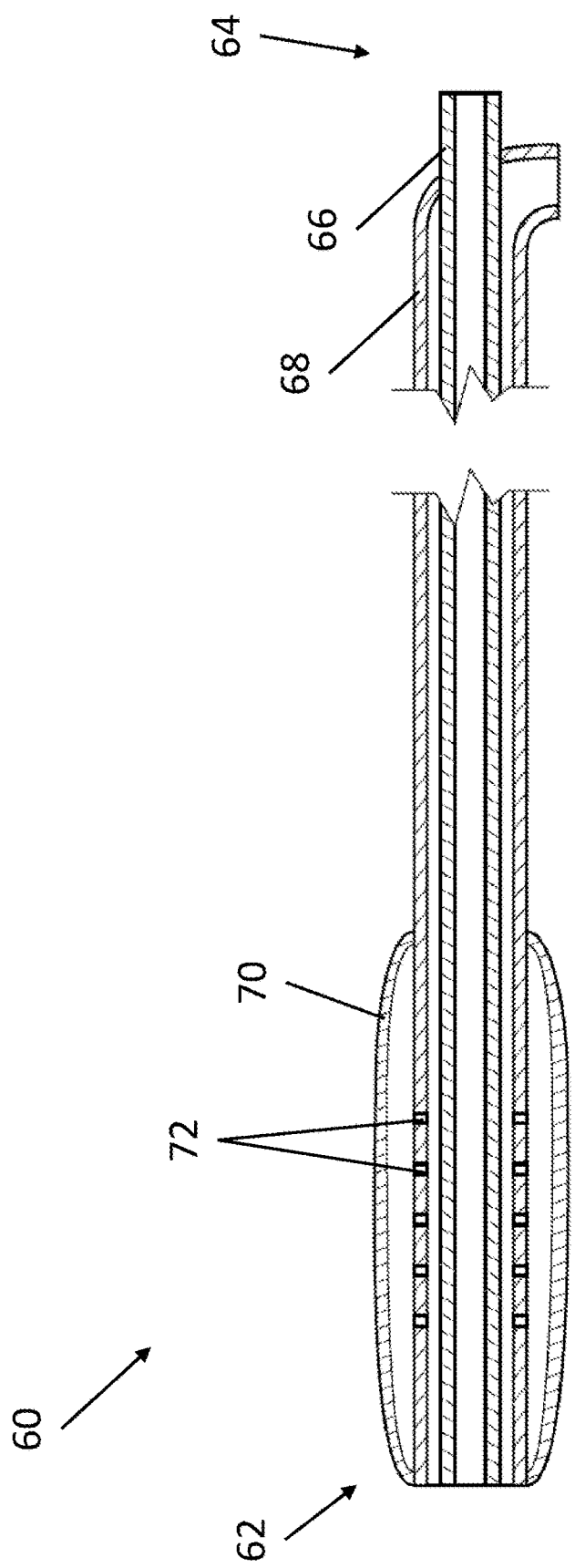
FIG. 8 depicts a side cross section view of an exemplary super-elastic balloon catheter in a collapsed configuration.

Referring now to FIG. 8, an exemplary super-elastic balloon catheter 60 is depicted. Super-elastic balloon catheter 60 has a distal end 62 and a proximal end 64 and comprises catheter 66, inflation tube 68, and super-elastic balloon 70. Inflation tube 68 is fluidly connected to super-elastic balloon 70 by a plurality of apertures 72.

Catheter 66 fits within the lumen of inflation tube 68. Catheter 66 is dimensioned to fit any suitable medical instrument, such as radiotherapy pellets, imaging devices, syringes, microsurgical devices, and the like. Catheter 66 may be open or closed at its distal end.

Figure 9:
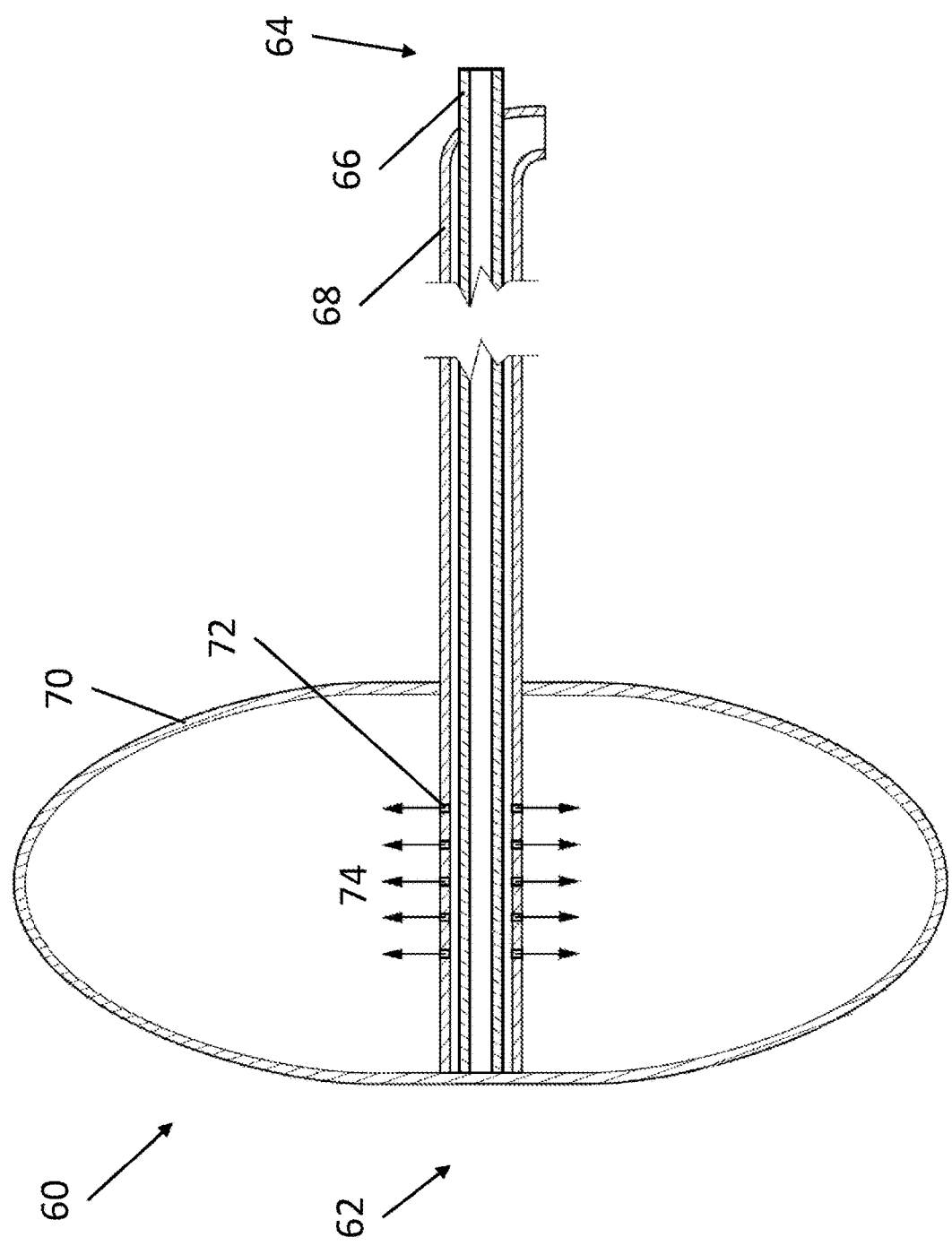
FIG. 9 depicts a side cross section view of an exemplary super-elastic balloon catheter in a fully deployed configuration.

Super-elastic balloon 70 can comprise any suitable material that can withstand pressure from being inflated. For example, super-elastic balloon 70 may comprise materials including but not limited to: rubber, silicone, nylon, PET, polyurethane, and the like. Super-elastic balloon 50 preferably comprises a material having high elasticity such that it possesses the capacity to expand greatly upon inflation (such as in FIG. 9) and to conform to the shape of the body cavity within which it is positioned. In one embodiment, super-elastic balloon 70 can have a substantially uniform material thickness. In another embodiment, super-elastic balloon 70 can have one or more regions of varying thickness, such that thinner regions have greater elasticity and thicker regions have less elasticity to promote directional expansion as desired. For example, super-elastic balloon 70 can have proximal regions comprising a thinner material than distal regions to promote directional expansion in the proximal direction.

Super-elastic balloon 70 is positioned at the distal end 62 of super-elastic balloon catheter 60. Super-elastic balloon 70 can be characterized as having a substantially donut shaped cross section having an inner "donut hole" formed by the inner surface of super-elastic balloon 70. Super-elastic balloon 70 is attached to super-elastic balloon catheter 60 such that the inner surface of super-elastic balloon 70 is joined to the distal outer surface of inflation tube 68. Super-elastic balloon 70 is inflated and deflated by inflation tube 68, wherein any suitable fluid (including but not limited to air, purified gas, water, saline and the like) enter and exit super-elastic balloon 70 through the plurality of apertures 72. In certain embodiments, super-elastic balloon 70 and inflation tube 68 are fluidly connected to catheter 66, such that fluids may be circulated through all three elements. For example, in certain embodiments wherein the fluid has a closely defined temperature, such as in thermotherapy, rapid circulation of fluid through super-elastic balloon 70, inflation tube 68, and catheter 66 enables the maintenance of the closely defined temperature.

Figure 10:
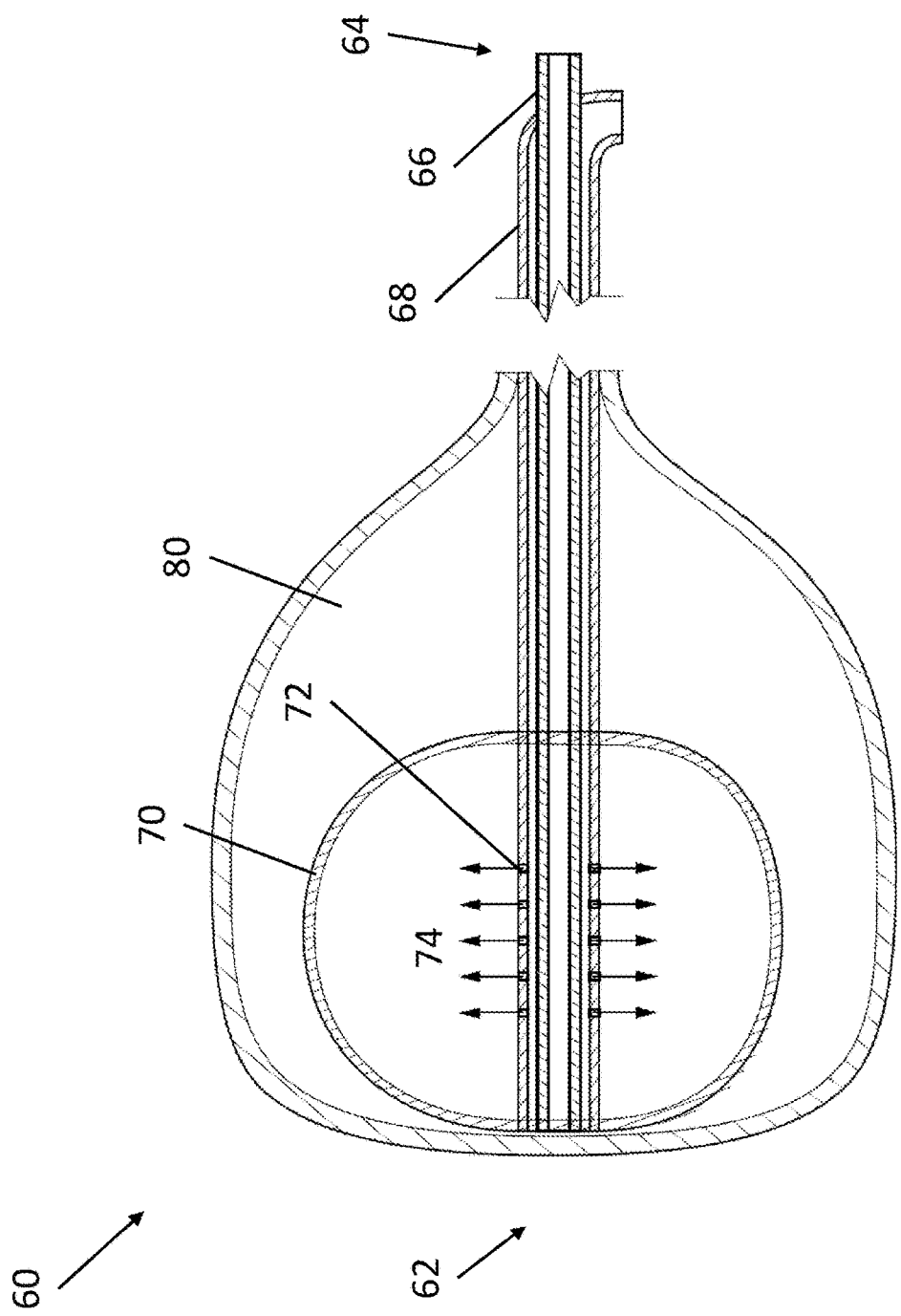
FIG. 10 depicts a side cross section view of an exemplary super-elastic balloon catheter partially deployed in a body cavity.
Figure 11:
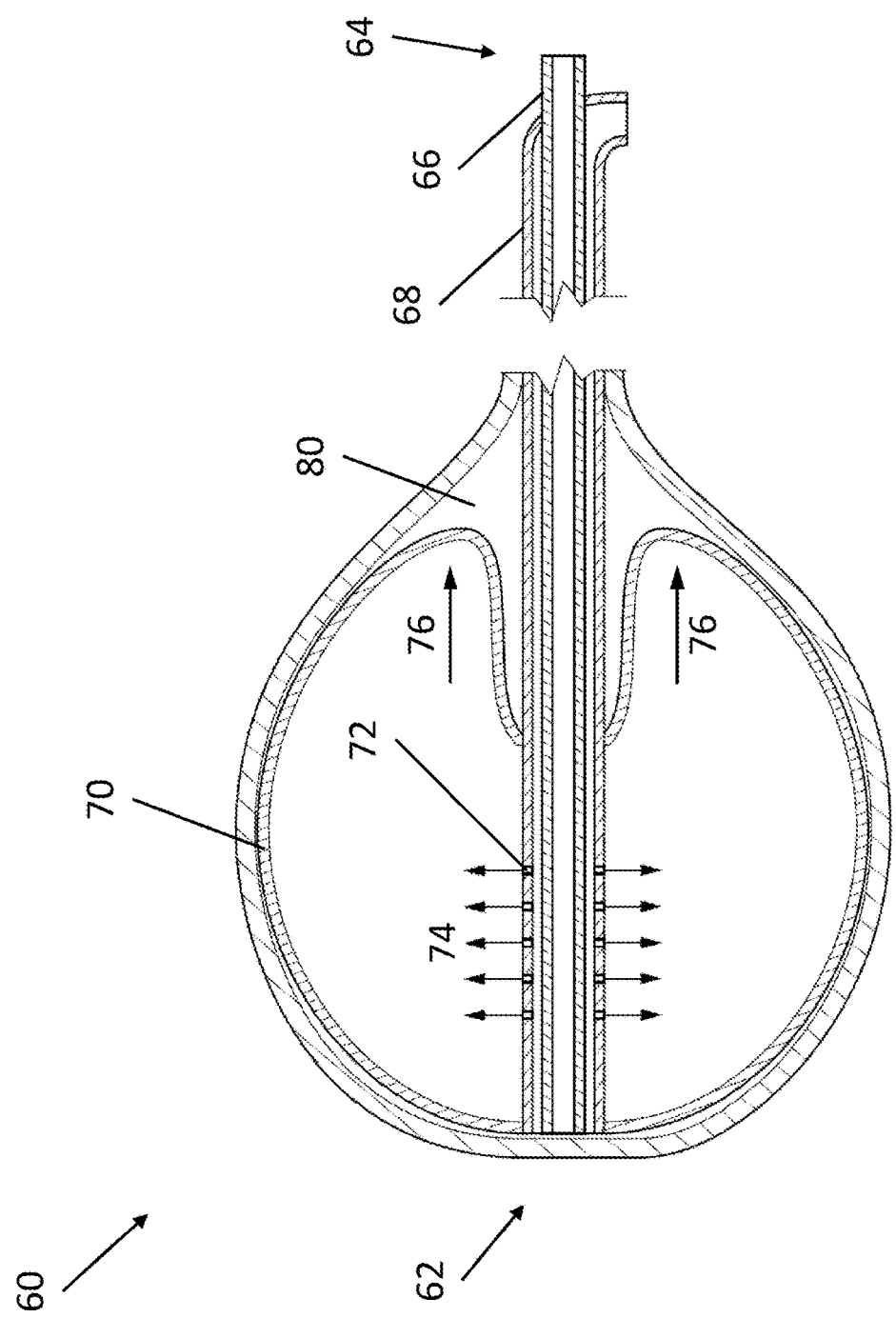
FIG. 11 depicts a side cross section view of an exemplary super-elastic balloon catheter fully deployed in a body cavity.

Referring now to FIG. 10 and FIG. 11, inflating super-elastic balloon 70 causes lateral expansion 74 of super-elastic balloon 70. Due to its high elasticity, further expansion of super-elastic balloon 70 forces it undergo proximal expansion 76 to conform to the confines of body cavity 80. Super-elastic balloon 70 does not expand in the distal direction due to being in contact with the body cavity wall.

Peripheral Catheter Balloon

Figure 12:
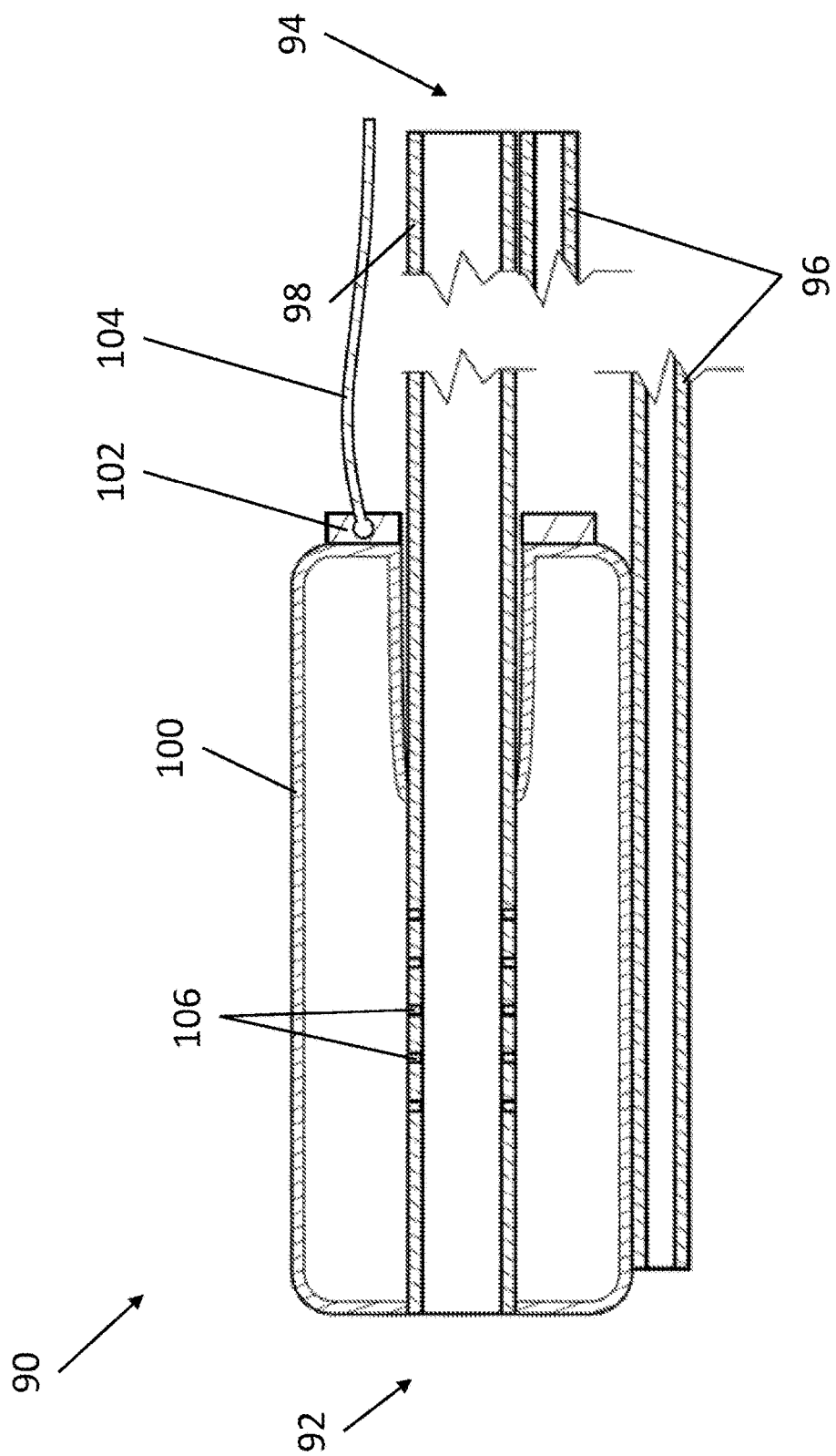
FIG. 12 depicts a side cross section view of an exemplary catheter having peripheral catheters in a partially collapsed configuration.

In various embodiments, any of the balloon catheters of the present invention may alternatively or additionally include peripheral catheters. Referring now to FIG. 12, by way of example, a sliding balloon catheter alternatively comprising peripheral catheters to form a peripheral balloon catheter 90 is depicted. Peripheral balloon catheter 90 has a distal end 92 and a proximal end 94 and comprises inflation tube 98, sliding balloon 100, and at least one peripheral catheter 96. Sliding balloon 100 further comprises sliding ring 102 and ring adjustment member 104. Inflation tube 98 is fluidly connected to sliding balloon 100 by a plurality of apertures 108.

The at least one peripheral catheter 96 is attached to the outer surface of peripheral balloon catheter 90. In various embodiments, peripheral balloon catheter 90 may further comprise a catheter that fits within the lumen of inflation tube 98, similarly to the previous embodiments. The at least one peripheral catheter 96 is dimensioned to fit any suitable medical instrument, such as radiotherapy pellets, imaging devices, syringes, microsurgical devices, and the like. The at least one peripheral catheter 96 may be open or closed at its distal end. In one embodiment, the at least one peripheral catheter 96 may comprise apertures for releasing therapeutic agents, chemical agents, and the like. For ease of use, the at least one peripheral catheter 96 may be releasably attached to inflation tube 98 along its length proximal from sliding balloon 100.

Figure 13:
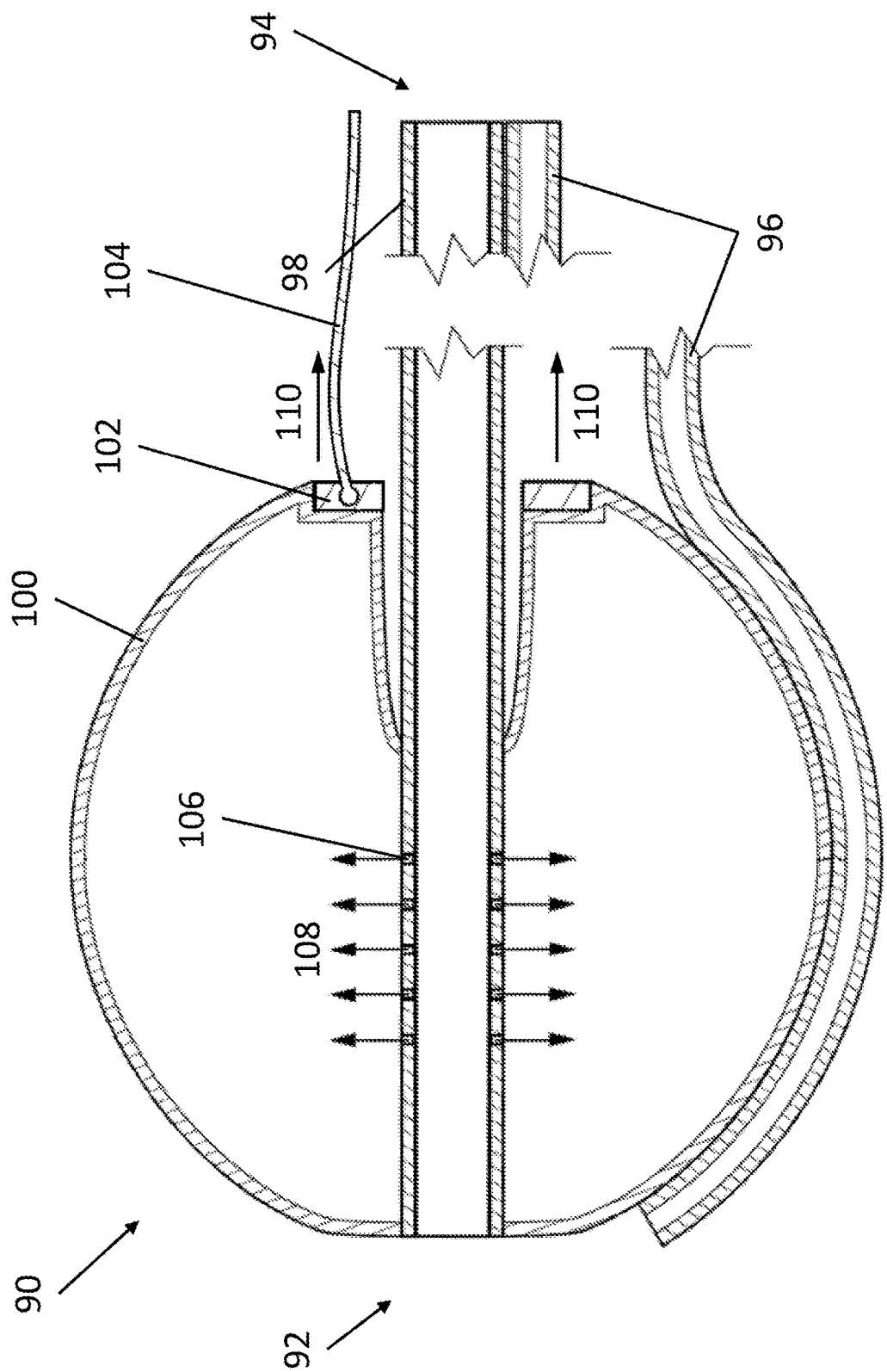
FIG. 13 depicts a side cross section view of an exemplary catheter having peripheral catheters in a fully deployed configuration.

The underlying balloon catheter retains all of its original functionalities. For example, as depicted in FIG. 12 and FIG. 13, the base sliding balloon catheter is able to inflate and deflate by inflation tube 98, wherein any suitable fluid (including but not limited to air, purified gas, water, saline and the like) enter and exit preformed balloon 50 through the plurality of apertures 106. In certain embodiments, sliding balloon 100 and inflation tube 98 are fluidly connected to at least one peripheral catheter 96, such that fluids may be circulated through all three elements. For example, in certain embodiments wherein the fluid has a closely defined temperature, such as in thermotherapy, rapid circulation of fluid through sliding balloon 100, inflation tube 98, and the at least one peripheral catheter 96 enables the maintenance of the closely defined temperature.

Inflating sliding balloon 100 allows lateral expansion 108 and proximal expansion 110 of sliding balloon 100. The at least one peripheral catheter 96, by virtue of being attached to the outer surface of sliding balloon 100, also undergoes lateral movement. In some embodiments, it may be advantageous for the at least one peripheral catheter 96 to comprise an elastic material such that it may lengthen to conform to the expanding balloon. Proximal expansion 110 of sliding balloon 100, as well as proximal movement of sliding ring 102 and ring adjustment member 104 in some embodiments, is unobstructed by the presence of the at least one peripheral catheter 96.

Tip-Loaded Balloon Catheter

Figure 14:
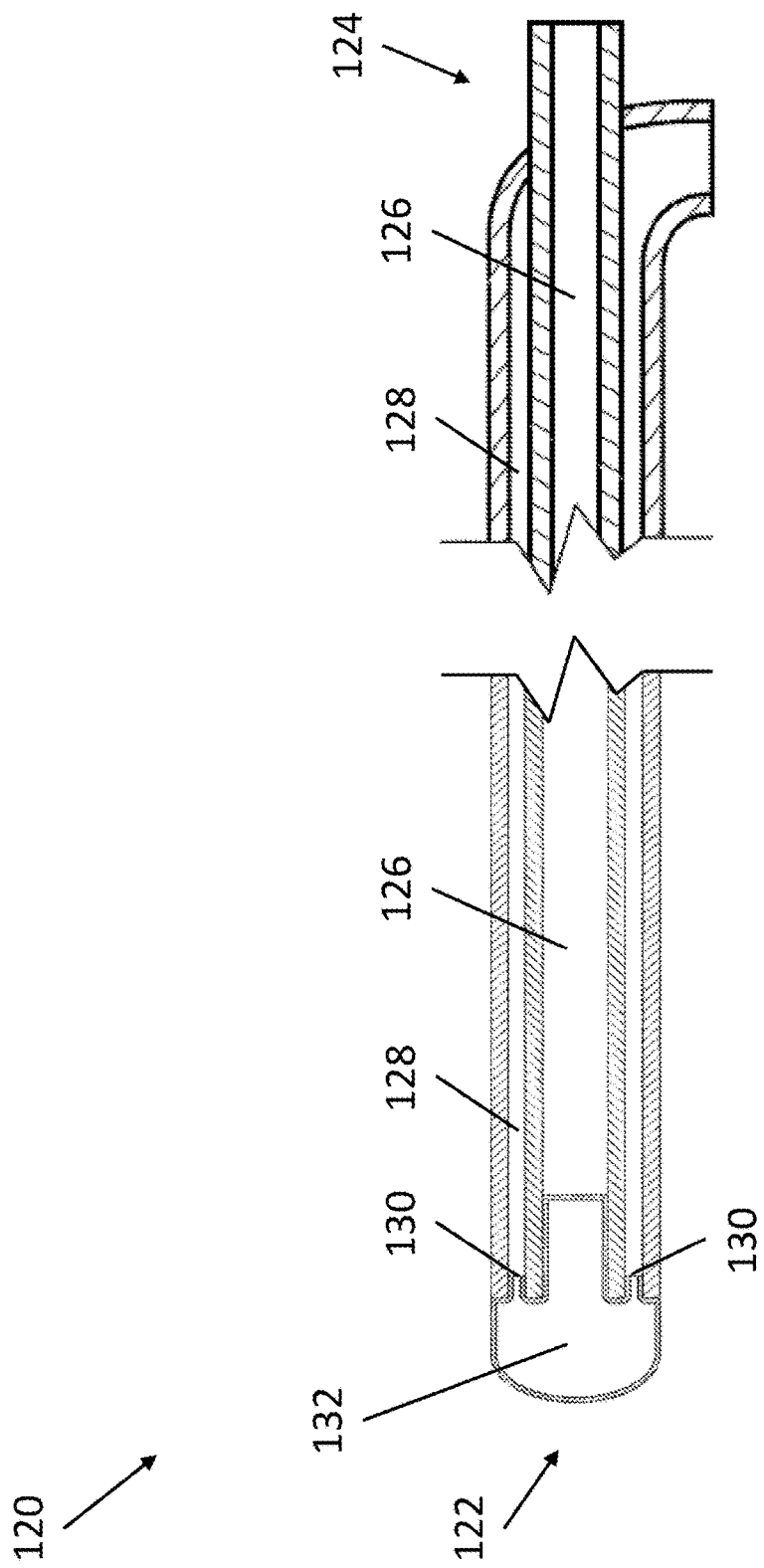
FIG. 14 depicts a side cross section view of an exemplary tip-loaded balloon catheter.

Referring now to FIG. 14, an exemplary tip-loaded balloon catheter 120 is depicted. Tip-loaded balloon catheter 120 has a distal end 122 and a proximal end 124 and comprises catheter 126, inflation tube 128, and tip-loaded balloon 132. Inflation tube 128 is fluidly connected to tip-loaded balloon 132 by a plurality of apertures 130.

Catheter 126 fits within the lumen of inflation tube 128. Catheter 126 is dimensioned to fit any suitable medical instrument, such as radiotherapy pellets, imaging devices, syringes, microsurgical devices, and the like. Catheter 126 may be open or closed at its distal end.

Tip-loaded balloon 132 is positioned at distal end 122. Tip-loaded balloon 132 can comprise any suitable material that can withstand pressure from being inflated. For example, tip-loaded balloon 132 may comprise materials including but not limited to: rubber, silicone, nylon, PET, polyurethane, and the like. In some embodiments, tip-loaded balloon 132 is molded to have a predetermined shape and retains its shape when expanded with minimal elasticity, so it may be advantageous for tip-loaded balloon 132 to comprise an inelastic material such as Mylar, or to be molded in slightly thicker material. In another embodiment, tip-loaded balloon 132 comprises a material having high elasticity such that it possesses the capacity to expand greatly upon inflation and to conform to the shape of the body cavity within which it is positioned. In one embodiment, tip-loaded balloon 132 can have a substantially uniform material thickness. In another embodiment, tip-loaded balloon 132 can have one or more regions of varying thickness, such that thinner regions have greater elasticity and thicker regions have less elasticity to promote directional expansion as desired. For example, tip-loaded balloon 132 can have proximal regions comprising a thinner material than distal regions to promote directional expansion in the proximal direction.

Tip-loaded balloon 132 is positioned at the distal end 122 of tip-loaded balloon catheter 120. In some embodiments, tip-loaded balloon 132 can be substantially stored within distal end 122, such as in a space directly adjacent to the distal end of catheter 126. Freeing the sides of tip-loaded balloon catheter 120 from any attached structures enables the overall outer diameter of tip-loaded balloon catheter 120 to be smaller than comparable catheters. In some embodiments, the flush side profile of tip-loaded balloon catheter 120 enables the device to accommodate a larger inner diameter catheter 126 while maintaining an overall outer diameter that does not exceed comparable catheters. Tip-loaded balloon 132 is inflated and deflated by inflation tube 128, wherein any suitable fluid (including but not limited to air, purified gas, water, saline and the like) enter and exit tip-loaded balloon 132 through the plurality of apertures 130. In certain embodiments, tip-loaded balloon 132 and inflation tube 128 are fluidly connected to catheter 126, such that fluids may be circulated through all three elements. For example, in certain embodiments wherein the fluid has a closely defined temperature, such as in thermotherapy, rapid circulation of fluid through tip-loaded balloon 132, inflation tube 128, and catheter 126 enables the maintenance of the closely defined temperature.

Figure 15:
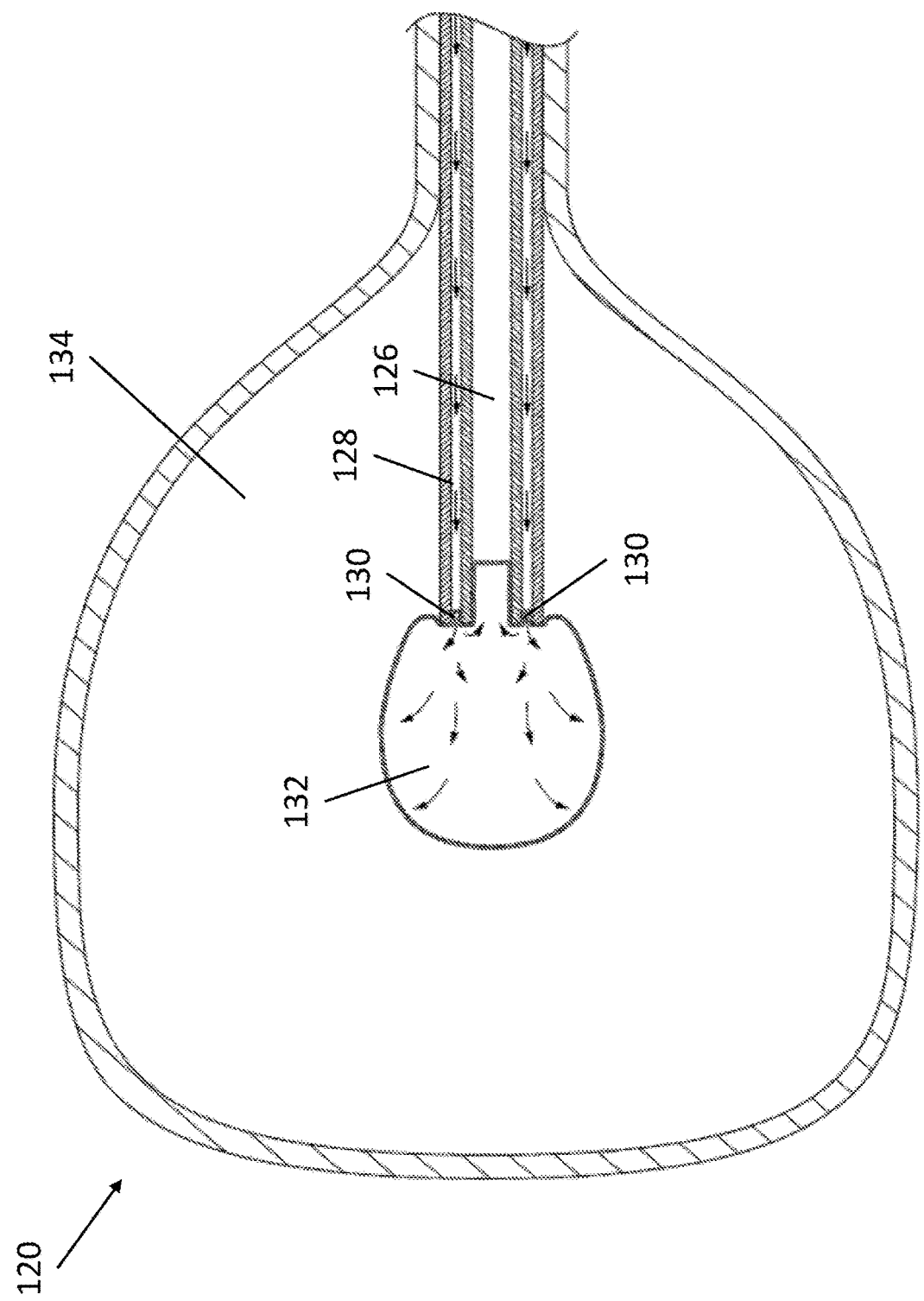
FIG. 15 depicts a side cross section view of an exemplary tip-loaded balloon catheter in a partially deployed configuration.
Figure 16:
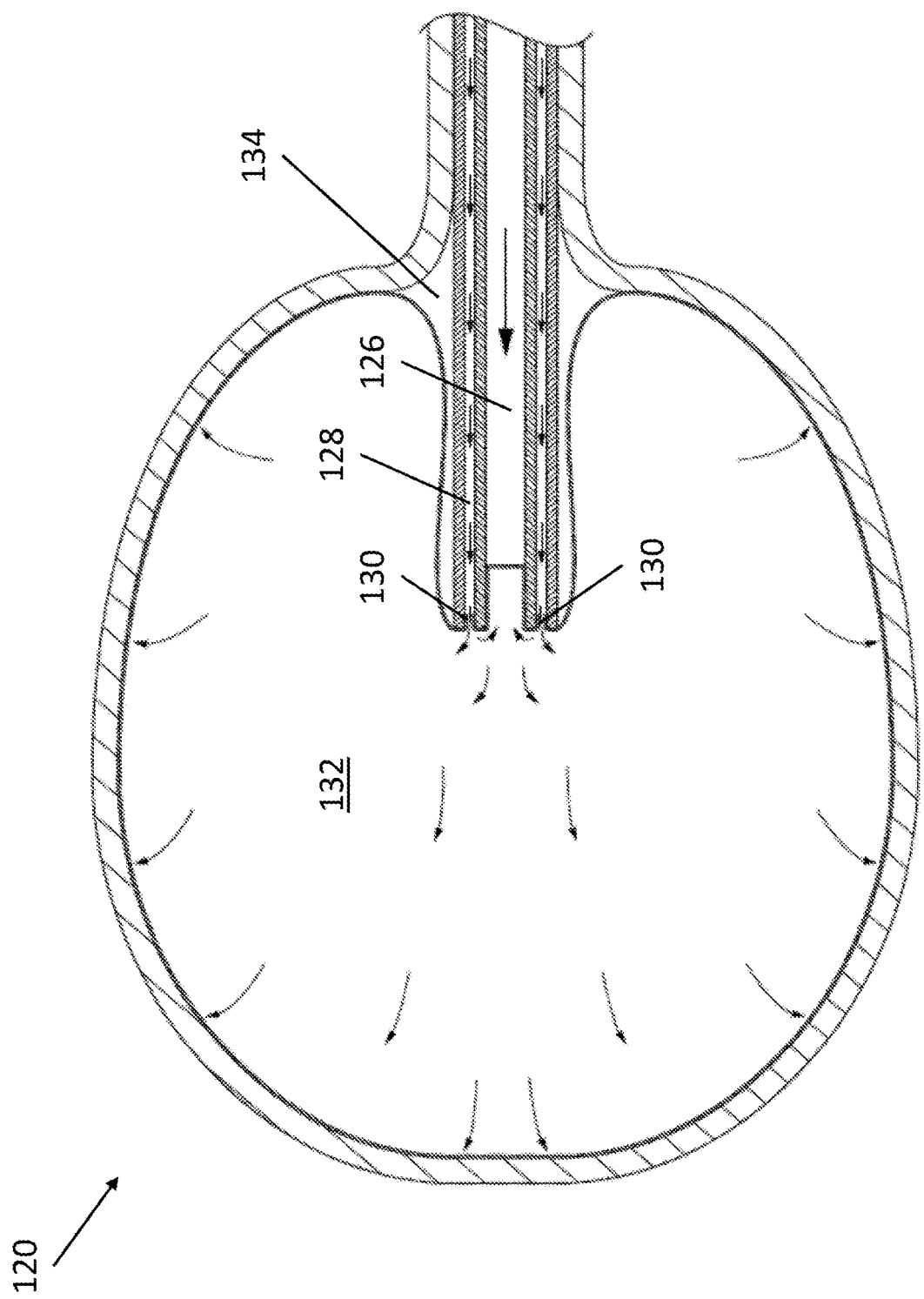
FIG. 16 depicts a side cross section view of an exemplary tip-loaded balloon catheter in a fully deployed configuration.
Figure 17:
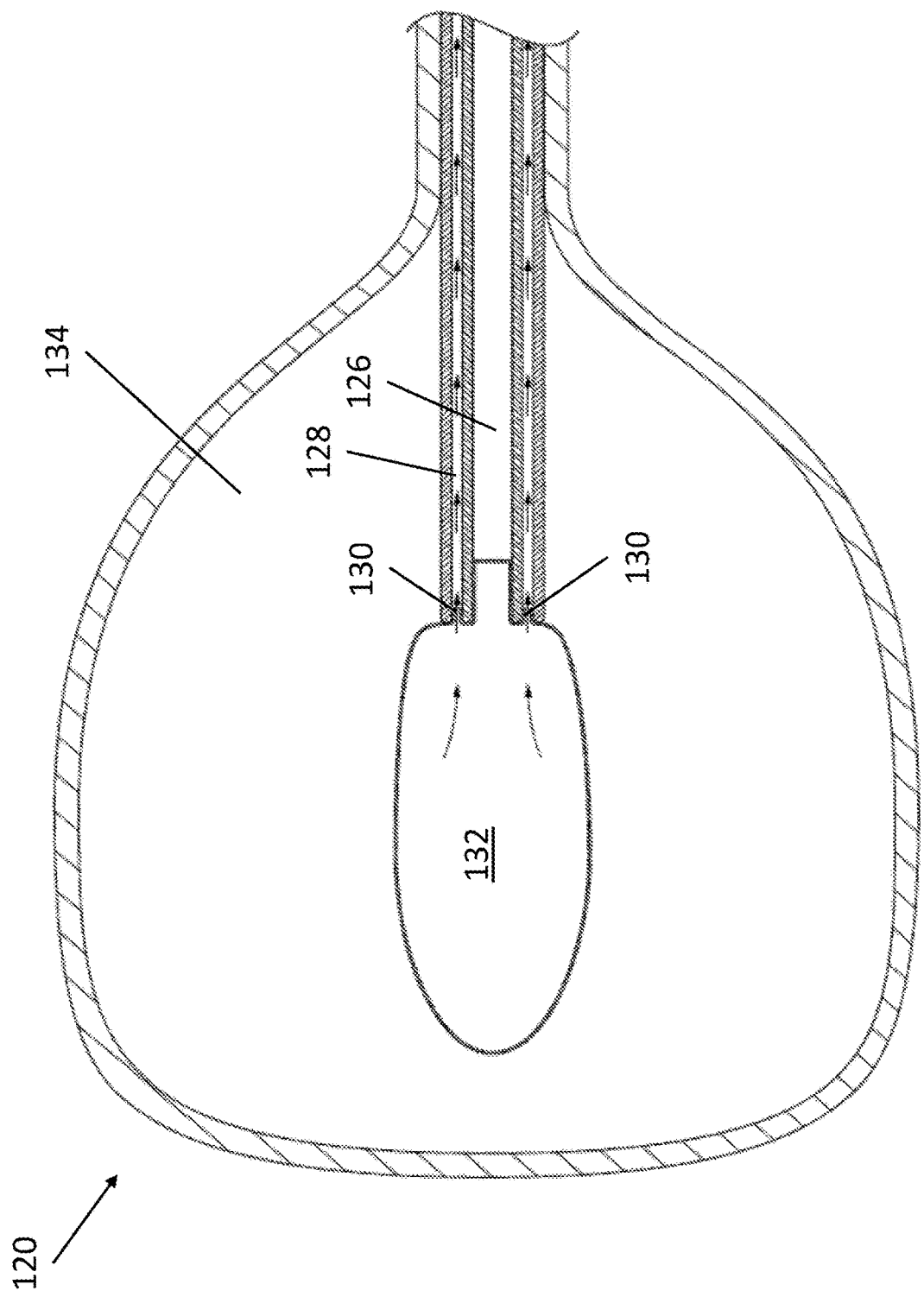
FIG. 17 depicts a side cross section view of an exemplary tip-loaded balloon catheter ready for extraction post-deployment.

Referring now to FIG. 15 and FIG. 16, inflating tip-loaded balloon 132 expands tip-loaded balloon 132 to fill and conform to the confines of body cavity 134. Referring now to FIG. 17, tip-loaded balloon 132 has been deflated prior to extraction. Tip-loaded balloon 132 does not have to be fully deflated to extract tip-loaded balloon catheter 120 from a patient because after a certain level of deflation, tip-loaded balloon 132 will have a diameter smaller than the outer diameter of tip-loaded balloon catheter 120. In contrast, conventional catheters having balloons attached at their sides may have to be fully deflated in order to minimize the overall outer diameter of the balloon catheter for extraction from a patient.

Methods of Use

The invention provides methods for using the balloon catheters of the present invention. In one embodiment, the methods relate to the insertion of any of the balloon catheters into any body cavity. In another embodiment, the methods relate to the insertion of any of the balloon catheters into the bladder to treat a disease, such as via brachytherapy.

Figure 18:
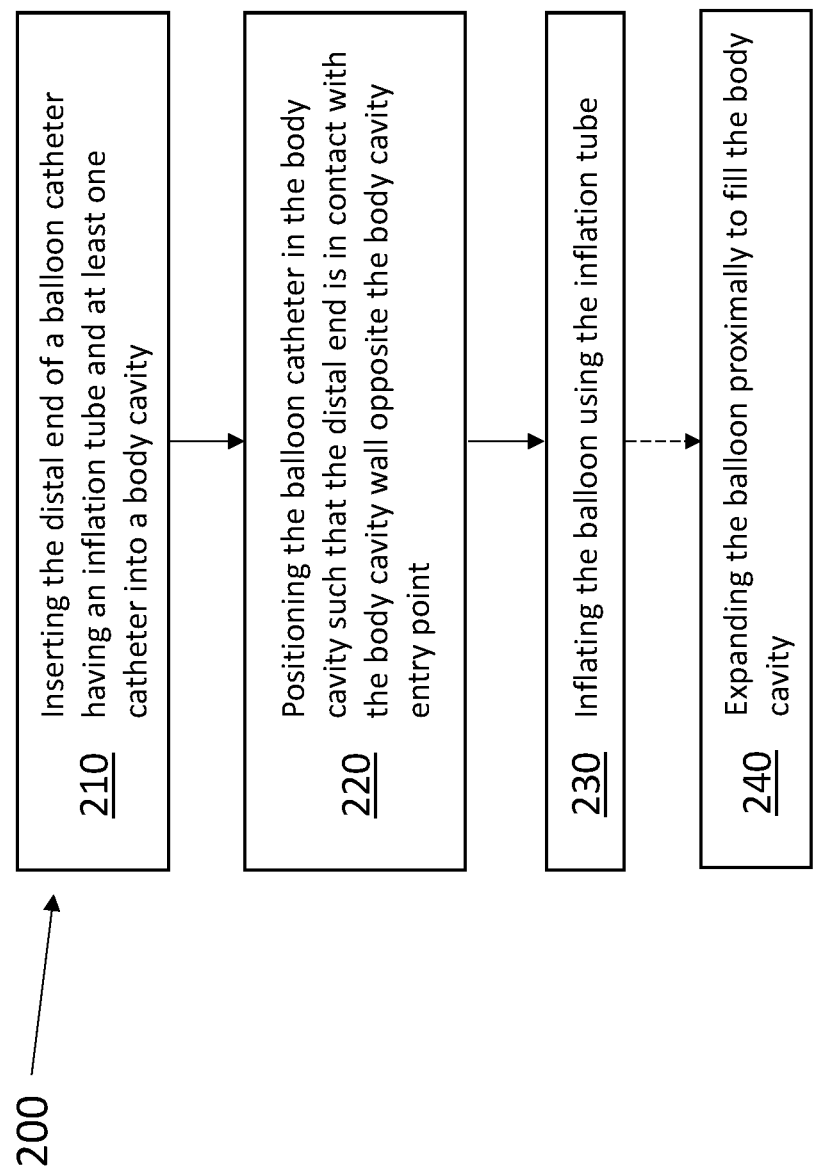
FIG. 18 is a flowchart depicting an exemplary method of inserting a balloon catheter into a body cavity.

In one embodiment, the methods relate to the insertion of any of the balloon catheters of the present invention into any body cavity. Referring now to FIG. 18, an exemplary method 200 of inserting a balloon catheter into a body cavity is depicted. Method 200 begins with step 210, wherein a balloon catheter having an inflation tube and at least one catheter is inserted into a body cavity. In step 220, the balloon catheter is positioned in the body cavity such that the distal end of the balloon catheter is in contact with the body cavity wall opposite of the body cavity entry point (such as in FIG. 10). In step 230, the balloon is inflated using the inflation tube. In step 240, the balloon is expanded proximally to fill the body cavity.

With a balloon catheter inserted into a body cavity, any suitable medical device may be inserted into the at least one catheter to carry out an appropriate treatment or medical procedure. For example, the balloon catheter is amenable to medical devices used in radiotherapy, thermotherapy, chemotherapy, laparoscopy, drug delivery, immunotherapy, brachytherapy, electronic brachytherapy, and the like.

Figure 19:
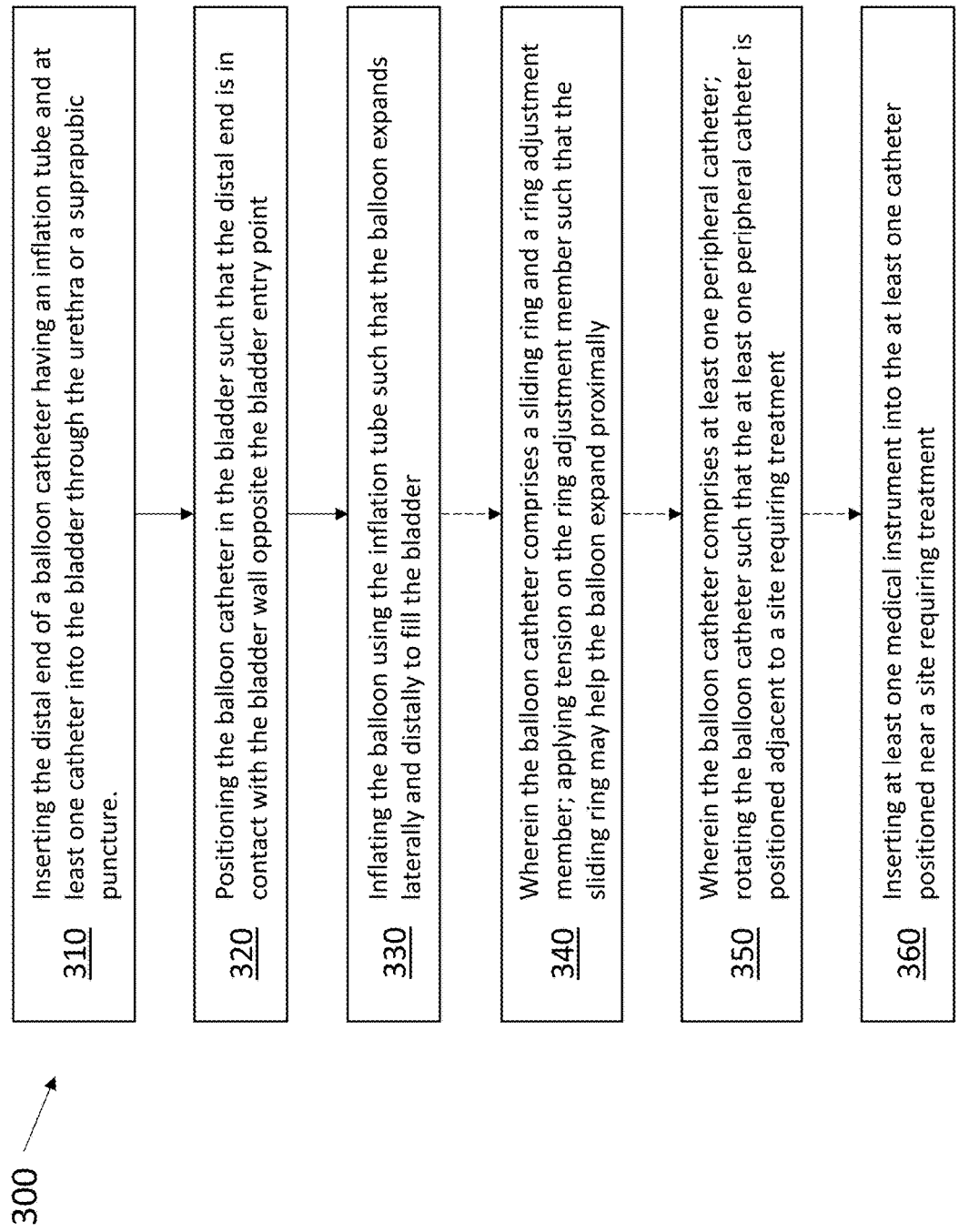
FIG. 19 is a flowchart depicting an exemplary method of inserting a balloon catheter into a bladder for treatment or a medical procedure.

In another embodiment, the methods relate to the insertion of any of the balloon catheters of the present invention into a bladder. Referring now to FIG. 19, an exemplary method 300 of inserting a balloon catheter into a bladder is depicted. Method 300 begins with step 310, wherein the distal end of a balloon catheter having an inflation tube and at least one catheter is inserted into the bladder. The balloon catheter may be inserted through the urethra or through a suprapubic puncture. In step 320, the balloon catheter is positioned in the bladder such that the distal end is in contact with the bladder wall opposite from the bladder entry point (such as in FIG. 10). In step 330, the balloon is inflated using the inflation tube. In step 340, the balloon is expanded proximally to fill the bladder. Optionally in step 340, wherein the balloon catheter comprises a sliding ring and a ring adjustment member, tension may be applied on the ring adjustment member such that the sliding ring attached to the proximal end of the balloon may help the balloon expand proximally. Optionally in step 350, wherein the balloon catheter comprises at least one peripheral catheter, the balloon catheter may be rotated within the bladder such that the at least one peripheral catheter is positioned adjacent to a site requiring treatment. Finally, in step 360, at least one medical instrument may be inserted into the at least one catheter positioned near a site requiring treatment to carry out the appropriate treatment or procedure.

In one embodiment, the treatment or procedure performed is radiotherapy. For instance, the procedure may be radiotherapy. The dose provided by the radiotherapy will depend on the location and duration of treatment. The radioactive source can be a radioisotope pellet or x-ray tube in the kV range, or any other mechanism of radiation emission.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:
1. A sliding balloon catheter device comprising:
an inflation tube having a lumen, a distal end and a proximal end;
at least one catheter positioned within the lumen of the inflation tube sharing a distal end with the inflation tube; and a balloon at least partially attached along its length to the distal end of the inflation tube and fluidly connected to the inflation tube, wherein the balloon comprises a proximal portion, including a proximal end, that is free from attachment to an outer surface of the inflation tube, such that the balloon is configured to be expandable proximally along the catheter;

wherein the balloon further comprises a sliding ring attached to the proximal end of the balloon that encircles the exterior of the inflation tube such that pulling on the sliding ring pulls the proximal end of the balloon in a proximal direction.

2. The device of claim 1, wherein the sliding ring has an adjustable circumference.

3. The device of claim 1, further comprising a ring adjustment member attached to the sliding ring.

4. The device of claim 1, further comprising at least one peripheral catheter attached to the exterior of the balloon.

5. The device of claim 1, wherein the balloon comprises a material selected from the group consisting of: rubber, silicone, nylon, polyethylene terephthalate (PET), and polyurethane.

6. The device of claim 1, wherein the balloon comprises a uniform material thickness.

7. The device of claim 1, wherein the balloon comprises one or more regions of varying material thickness.

8. The device of claim 1, wherein the balloon, the inflation tube, and the at least one catheter are fluidly connected.

9. The device of claim 1, wherein the balloon conforms to the shape of a body cavity when fully inflated.

10. The device of claim 1, wherein the balloon is a preformed, substantially inelastic balloon.

11. The device of claim 1, wherein the balloon is attached at a distal tip of the inflation tube.

12. A method of inserting a balloon catheter into a body cavity, comprising the steps of:

inserting the distal end of a balloon catheter having a balloon, an inflation tube and at least one catheter into the body cavity;

positioning the balloon catheter in the body cavity such that the distal end is in contact with the body cavity wall opposite a body cavity entry point and wherein a sliding ring is attached to the proximal end of the balloon, wherein the proximal end of the balloon encircles the exterior of the inflation tube;

inflating the balloon with a fluid using the inflation tube, such that a proximal portion of the balloon, including the proximal end, that is free from attachment to an outer surface of the inflation tube expands proximally to fill the body cavity; and applying tension on a ring adjustment member, such that the sliding ring pulls the proximal end of the balloon in a proximal direction.

13. The method of claim 12, wherein the fluid is one of a liquid or a gas.

14. The method of claim 12, wherein the balloon catheter further comprises at least one peripheral catheter.

15. The method of claim 14, further comprising the step of rotating the balloon catheter such that the at least one peripheral catheter is positioned adjacent to a site requiring treatment.

16. The method of claim 12, further comprising the step of inserting medical instruments into the at least one catheter positioned near a site requiring treatment.

17. The method of claim 16, wherein the treatment is selected from the group consisting of: radiotherapy, thermotherapy, chemotherapy, laparoscopy, drug delivery, and immunotherapy.

18. The method of claim 16, wherein the at least one medical instrument is selected from the group consisting of: a radiotherapy pellet, an imaging device, a syringe, and a microsurgical device.

19. The method of claim 12, wherein the body cavity is a bladder and the distal end of the balloon catheter is inserted into the bladder through the urethra or a suprapubic puncture.

* * * * *